(12) United States Patent
Woolfson et al.

(10) Patent No.: US 9,033,901 B2
(45) Date of Patent: May 19, 2015

(54) SYSTEM FOR DETERMINING INDIVIDUAL USER ANTHROPOMETRIC CHARACTERISTICS RELATED TO MATTRESS PREFERENCE

(76) Inventors: David Woolfson, Bray (IE); Duncan Bain, Kings Langley (GB); Lee Hubbard, Luton (GB)

(*) Notice: Subject to any disclaimer, the term of this patent is extended or adjusted under 35 U.S.C. 154(b) by 380 days.

(21) Appl. No.: 12/885,707

(22) Filed: Sep. 20, 2010

(65) Prior Publication Data

US 2011/0009776 A1  Jan. 13, 2011

Related U.S. Application Data

(63) Continuation of application No. 11/897,095, filed on Aug. 29, 2007, now abandoned.

(51) Int. Cl.
*A61B 5/107* (2006.01)
*G01F 17/00* (2006.01)
*G01B 11/28* (2006.01)
*A61B 5/00* (2006.01)

(52) U.S. Cl.
CPC .............. *A61B 5/1077* (2013.01); *G01F 17/00* (2013.01); *G01B 11/28* (2013.01); *A61B 5/1073* (2013.01); *A61B 5/1079* (2013.01); *A61B 5/4561* (2013.01)

(58) Field of Classification Search
CPC .... A61B 5/0064; A61B 5/0073; A61B 5/107; A61B 5/1073; A61B 5/1077; A61B 5/1079; G01B 11/28; G01B 11/285; G01F 17/00

USPC .................. 600/595, 587; 345/473, 169, 464; 348/169; 359/464

See application file for complete search history.

(56) References Cited

U.S. PATENT DOCUMENTS

| | | | |
|---|---|---|---|
| 5,515,168 A | 5/1996 | Dudkiewicz | |
| 5,956,525 A | 9/1999 | Minsky | |
| 6,580,405 B1 | 6/2003 | Yamazaki et al. | |
| 7,184,047 B1 | 2/2007 | Crampton | |
| 2004/0155962 A1 | 8/2004 | Marks | |
| 2005/0272517 A1 | 12/2005 | Funk et al. | |
| 2006/0001760 A1* | 1/2006 | Matsumura et al. | 348/335 |

FOREIGN PATENT DOCUMENTS

| | | |
|---|---|---|
| DE | 3638941 | 11/1986 |
| DE | 102004001182 | 1/2004 |
| JP | 2000083928 | 3/2000 |
| WO | 0137692 | 5/2001 |

* cited by examiner

*Primary Examiner* — Max Hindenburg
*Assistant Examiner* — John Pani
(74) *Attorney, Agent, or Firm* — K&L Gates LLP

(57) ABSTRACT

A measuring device to aid mattress selection has an upstanding frame with a plurality of vertically space-apart horizontal illuminated strips. A camera mounted in front of the frame takes front view and side view images of a person standing in front of the illuminated strips. These images are delivered to an associated computer having means to determine the body mass distribution and the spine curvature of the person based on the images of the strips taken by the camera and in particular based on those portions of the image of the illuminated strips blocked by the person standing in front of the illuminated strips. This information can then be used to aid in appropriate mattress selection for the person.

10 Claims, 5 Drawing Sheets

SYSTEM FOR DETERMINING INDIVIDUAL USER ANTHROPOMETRIC CHARACTERISTICS RELATED TO MATTRESS PREFERENCE

BACKGROUND OF THE INVENTION

Field of the Invention

This invention relates to a device and system for determining individual user anthropometric characteristics related to mattress preference

Introduction

When buying or choosing a mattress, there is currently little information to guide the user, in terms of selecting a mattress that will suit his/her particular body characteristics. Mattresses are presented as a general range from basic quality to high quality, with no account taken of the particular physique of the user, and no attempt to match mattress characteristics to the physical characteristics of the user. This contrasts sharply with, for example, the selection process for shoes: physical characteristics of the user including foot length, width, and arch height are taken into account when selecting the shoe, and shoes are categorised according to the relevant parameters.

Recent research (Bain 2006) has indicated that certain relationships exist between user physique and optimal mattress characteristics. For example, to maintain spinal alignment when lying on the side (generally recognised as desirable to prevent back pain) the optimal firmness of the mattress depends on the breadth from the saggital plane of bony prominences such as the greater trochanter and ilium, and on the body mass distribution of the user. The mattress needs to provide the correct amount of resistance to allow these bony prominences to displace into the mattress the correct distance to preserve a straight spine. The amount of resistance required depends on the user parameters mentioned.

When lying on the back, it is generally recognised that the natural curvature of the spine, including a lumbar curve, a thoracis curve, and a cervical curve, should be maintained for comfort. Once again, it has been shown that the optimal characteristics of the mattress to maintain these curves depends on the individual user shape. For example, a user with a tighter (smaller radius) lumbar curve may require a mattress with greater differential yield between adjacent regions of the mattress. This has implications, not only for the firmness of the mattress, but also in the spatial resolution (e.g. springs per square metre, or foam profile density) of the support, and the tensile properties of the top layers of padding. A mattress that is soft overall, but has a very coarse distribution of springs, or a stiff, hammock-like cover, will not be able to accommodate a tightly accentuated lumbar curve.

This invention relates to a simple and inexpensive device, requiring little precision in set-up or operation, for measuring and analysing the salient parameters of the individual user, for the purposes of assisting with mattress selection.

Description of the Related Art

Some steps have been taken previously in an attempt to provide information relating to the individual user, that may be used to inform the choice of mattress.

One example is pressure mapping. In this method, a pressure mapping device, consisting of a two-dimensional array of pressure sensors, is used to display a two-dimensional map of the pressure distribution on the skin of the user when lying on the mattress. Nominally, certain parameters in the mattress may be modified to optimise the pressure distribution. This method has a number of problems. One problem is that it is not well understood what would constitute a good or bad pressure distribution, in terms of maintaining a good posture. Current understanding and interpretation of pressure maps is focussed predominantly on the issue of pressure ulcers in hospital patients, and no is more concerned with locating areas of high pressure which may lead to poor skin perfusion. Strategies for adjusting inflation pressures to minimise peak pressure values may be effective in maintaining skin health, but will be of little value for maintaining good sleeping posture.

Furthermore, pressure mapping technologies are expensive, and the expense may be prohibitive in many retail establishments. A great deal of specialist scientific expertise is also required to maintain, calibrate, and operate pressure mapping systems in such a way as to obtain valid results. This level of expertise is very unlikely to be on hand in a retail context.

Patent Specification DE 102004001182 discloses a body measuring device to aid in mattress selection. This includes a scanning device for measuring body shape and a device which engages and rolls along the spine to determine the spine curvature. Another bed selecting device is disclosed in JP 2000083928 which includes a series of vertically spaced-apart rods which are advanced on a frame against a person's back to give an indication of spine curvature.

In Patent Publication No. WO 01/037692 there is disclosed a rotating dais upon which a person stands with a homogenously luminous panel behind the dais. A camera in front of the dais captures 92 silhouettes of the person as they are rotated through 360° on the dais. These silhouettes are used to calculate the volume and shape of the person on the dais. This information is used in the production of clothing articles to fit the person. Other body shape measurement systems are disclosed in DE 3638941, U.S. Pat. Nos. 5,515,168 and 5,956,525.

SUMMARY OF THE INVENTION

According to the invention there is provided a measuring device to aid mattress selection, including:
  a support frame,
  a plurality of illumination strips mounted spaced-apart on the support frame,
  a camera mounted in front of the frame having a lens directed at the illumination strips,
  a computer connected to the camera to receive images therefrom,
  said computer having means to determine one or more anthropometric characteristics of a person standing between the camera and the illumination strips based on images of the strips taken by the camera.

In one embodiment of the invention, the computer is operable to determine said one or more anthropometric characteristics based on those portions of an image of the illuminated strips blocked or obscured by the body of the person standing between the camera and the illuminated strips.

In a preferred embodiment of the invention, said anthropometric characteristics include body mass distribution and spine curvature of the person.

In one embodiment of the invention, the illuminated strips are operable to generate light of a particular colour and the camera is adapted to preferentially sensitive to said colour.

In another embodiment the illuminated strips are adapted to blink at a specified frequency and the computer is operable to compare an image received from the camera when the strips are illuminated with an image received from the camera when the strips are not illuminated in order to eliminate extraneous detail from the image resulting from ambient light.

In another embodiment the support frame is an upstanding frame and a plurality of horizontal illuminated strips are mounted vertically spaced-apart on the support frame.

In a further embodiment the camera is a personal computer web cam connected to a computer via USB.

In another embodiment the illuminated strips comprise electroluminescent wires.

In another embodiment the illuminated strips comprise fluorescent strip lights.

In another aspect the invention provides a measuring device, including:
  a support frame,
  a plurality of illumination strips mounted spaced-apart on the support frame,
  a camera mounted in front of the support frame having a lens directed at the illumination strips,
  a computer connected to the camera to receive images therefrom,
  said computer having means to determine one or more characteristics of a body mounted between the camera and the illumination strips based on images of the strips taken by the camera.

In a further aspect, the invention provides a method for determining individual user anthropometric characteristics, including:
  positioning said user between a set of spaced-apart illumination strips and a camera,
  illuminating said strips,
  taking an image of the illuminated strips and said user by means of the camera,
  delivering said image from the camera to an associated computer, and
  determining by means of said computer one or more preselected anthropometric characteristics of the user based on said image.

BRIEF DESCRIPTION OF THE DRAWINGS

The invention will be more clearly understood by the following description of some embodiments thereof, given by way of example only with reference to the accompanying drawings, in which.

DESCRIPTION OF THE PREFERRED EMBODIMENTS

Figure 1:
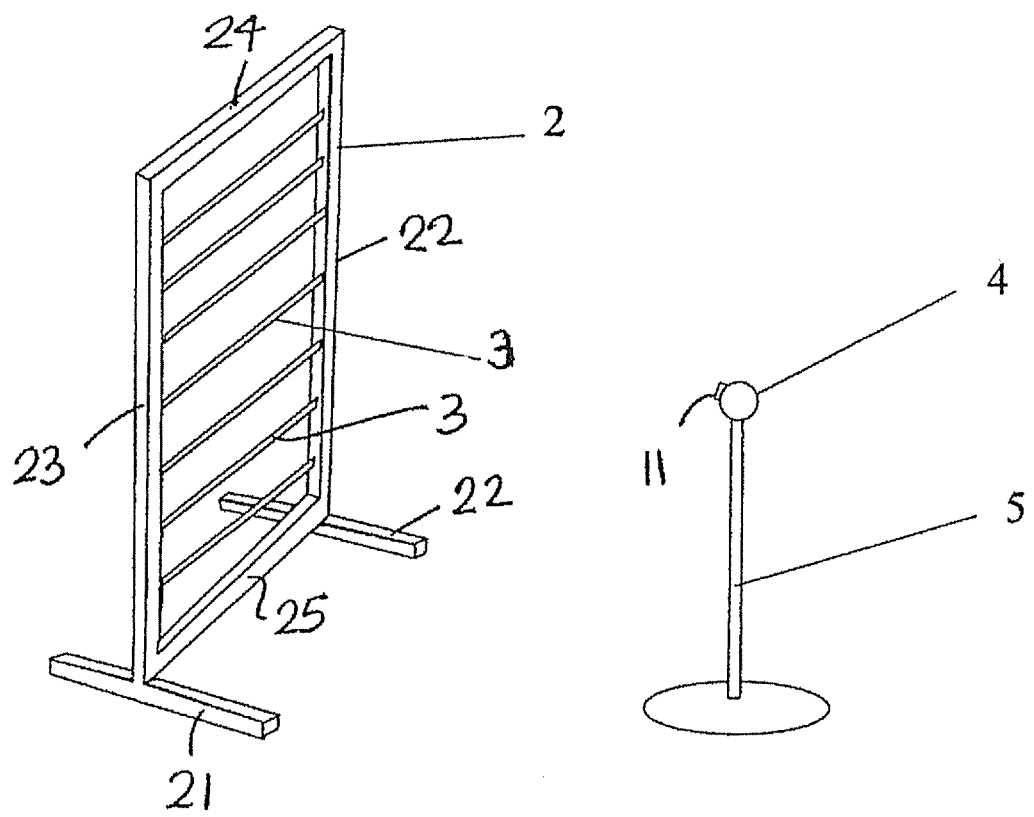
FIG. 1 is a diagrammatic perspective view of a measuring device to aid mattress selection according to the invention.

Referring to the drawings there is illustrated a measuring device to aid mattress selection according to the invention indicated generally by the reference number 1. The device 1 includes an upright standing frame, 2. This frame supports a number of spaced-apart horizontal illumination strips, 3. In one embodiment reduced to practice, these strips 3 consist of electroluminescent wire, of 2 mm thickness. However, it would be possible to construct a functional device for these purposes using different thicknesses of wire, or using other light sources such as fluorescent strip lights. The illumination strips 3 are connected to any suitable power source 35.

A camera 4 is mounted in front of the frame 2 and is provided with a stand 5 so that the camera 4 is oriented with all the illumination strips 3 horizontal in its view. A lens 11 of the camera 4 is directed at the illumination strips 3. The camera 4 is connected by a cable 14 and USB (Universal Series Bus) to an associated computer 6 which receives images generated by the camera 4. In one reduction to practice, the camera 4 is a personal computer web cam, connected to a computer 6 via USB. However, other types of camera 4 would be equally applicable.

The standing frame 2 has ground engaging legs 20, 21 supporting an upstanding rectangular frame having side members 22, 23 interconnected by a top member 24 and a bottom member 25. The illumination strips 3 are mounted horizontally between the side members 22, 23 and are vertically spaced-apart on the standing frame 2.

Figure 2:
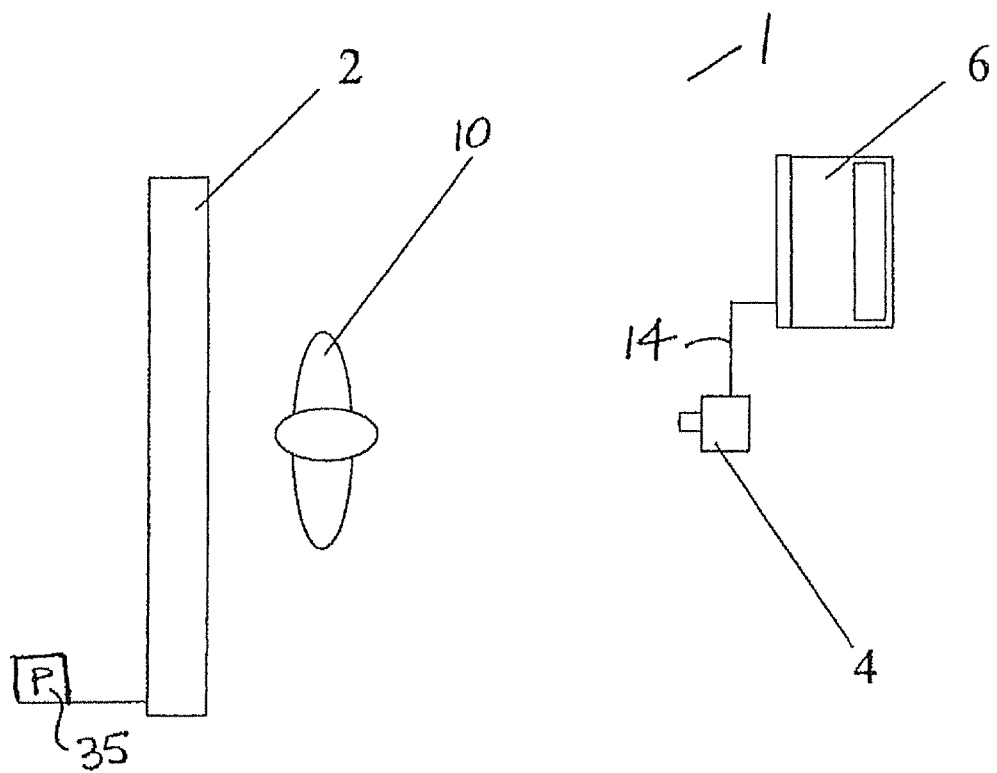
FIG. 2 is a diagrammatic plan view of the measuring device, shown in use.

FIG. 2 shows a plan view of the measuring device 1 in use carrying out a measurement procedure, with the standing frame 2, the camera 4, and the computer 6 to which the camera 4 is connected. A person 10 being measured stands in front of the illuminated strips 3. He stands first facing the camera 4 to give a frontal view, and one picture is taken. He then stands sideways, and a profile picture is taken.

Figure 3:
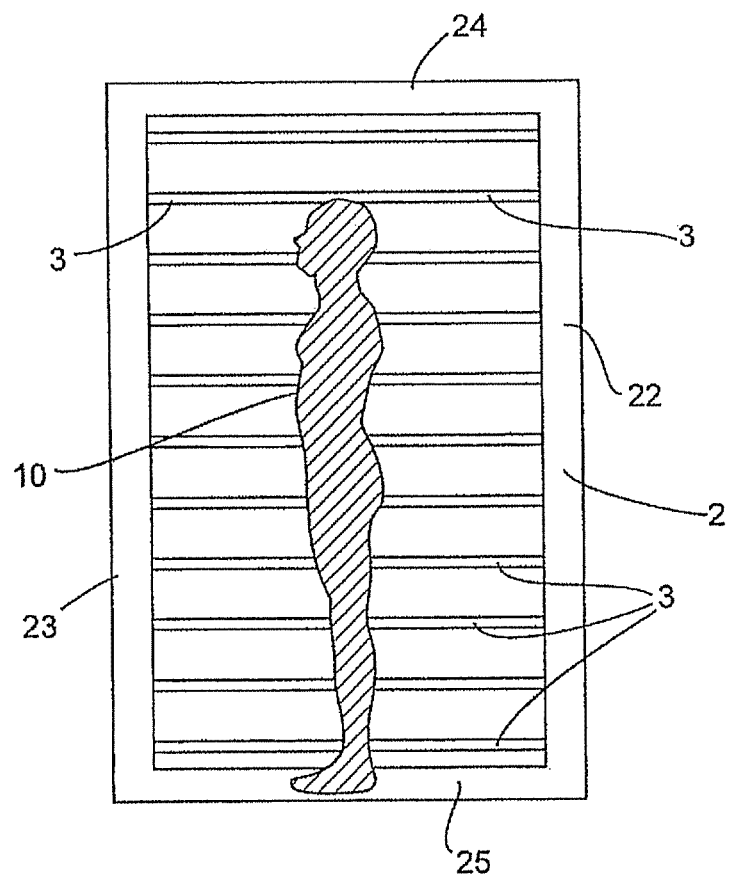
FIG. 3 is a side elevational view of portion of the device, shown in use.

FIG. 3 shows the profile view as seen by the camera 4, with the subject 10 standing in front of the illuminated strips 3.

Advantageously, the colour settings on the camera 4 can be set up to be preferentially sensitive to a particular colour of light emanating from the illuminated strips 3. In one embodiment, electroluminescent wire was chosen of an aqua blue colour, and the Red-Green-Blue (RGB) setting of the camera 4 were tuned to be preferentially sensitive to this colour. This technique is useful for eliminating the effects of ambient light, allowing the camera 4 to see exclusively the illuminated strips 3.

Also advantageously, the illuminated strips 3 may be set up to blink at a specified frequency, and the computer 6 may be programmed to compare frames received from the camera 4 when the strips 3 are illuminated with those received from the camera 4 when the strips 3 are not illuminated. This technique is also useful for eliminating extraneous detail from the image resulting from ambient light.

Figure 4:
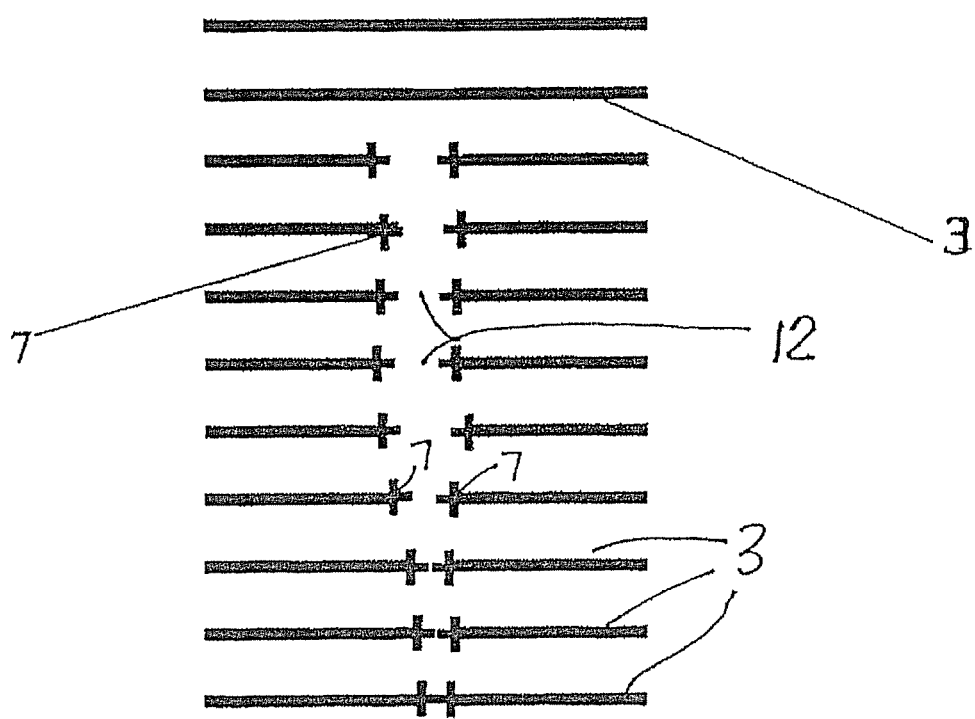
FIG. 4 shows a camera image recorded by the device.

FIG. 4 shows those sections of illuminated strip 3 visible in an image 30 received by the camera 4. It can be seen that missing segments 12 of illuminated strip 3 relate to the profile of the subject 10 standing in front of the illuminated strips 3.

A simple edge-detection algorithm is employed in software in the computer 6 to identify the beginning and end 7 of each missing segment 12. This results in a plot on the computer 6 of the width in pixels of the broken sections of each illuminated strip 3.

Since the vertical distance between strips 3 is known, and the overall width of strips 3 is also known, this information may be used for real-time calibration (in software on the computer 6) to calculate the absolute width of the broken sections of illuminated strip 3 from the number of pixels, by simple scaling. More sophisticated calibration routines may be employed to account for parallax effects, or perspective or "fish-eye" effects, but for practical purposes these have not been found to be necessary.

Figure 5:
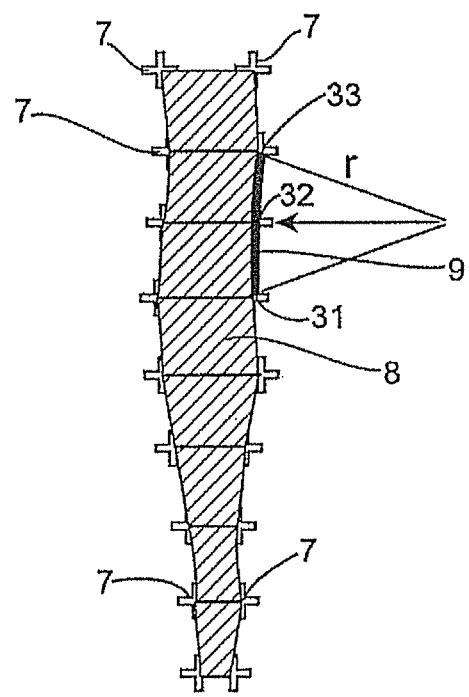
FIG. 5 is an illustration of a body mass distribution representation generated by the device.

Referring to FIG. 5, the known spatial locations of the points, 7, demarcating each broken illuminated segment 12, allow the delineation of a series of polygons, 8, characterising the body shape.

Additionally, any three vertically adjacent points 31, 32, 33 may be used to calculate a radius of curvature, by the simple method of taking chords. This is very easily achieved in software. By this means, maximal positive and negative curvatures may be identified.

Since the information as presented in FIG. 5 is available for both the front and side views on the subject 10, approximations can be made of the volume (and therefore mass) of each polygonal section. This provides information as to the distribution of body mass of the subject 10.

Based on knowledge of the mass distribution and curvature parameters, more informed recommendations may be made for mattress selection.

In a further embodiment, the device is coupled to a database, which updates with each new scan to retain the relevant parameters of each user scanned. Ultimate mattress preference may also be input as a field. This allows for future neural network training or other form of learning to determine the optimal set of rules to relate the measured parameters to mattress choice.

In a further embodiment, information from the above parameters may be used to determine an advisory inflation pressure for adjustable air mattresses.

In this specification the terms comprise, comprises, comprised and comprising or any variation thereof and the terms include, includes, included or including or any variation thereof are considered to be totally interchangeable and they should all be afforded the widest possible interpretation.

The invention is not limited to the embodiments hereinbefore described which may be varied in construction and detail within the scope of the appended claims.

The invention claimed is:

1. A measuring device for determining individual user anthropometric characteristics related to mattress preference to aid mattress selection, including:
   a support frame,
   a plurality of illumination strips mounted spaced-apart on the support frame,
   a camera mounted in front of the frame having a lens directed at the illumination strips with said illumination strips in its view,
   a computer connected to the camera to receive images of the illumination strips from said camera,
   said computer having means to determine one or more anthropometric characteristics of a person standing between the camera and the illumination strips in a front view and in a side view based on images of the illumination strips taken by the camera when said illumination strips are illuminated,
   said computer being operable to determine said one or more anthropometric characteristics based on those portions of images of the illuminated strips blocked by the person standing between the camera and the illuminated strips in said front view and said side view and the distance between the illumination strips,
   said anthropometric characteristics including body mass distribution determined by delineation of a series of polygons characterising the body shape of said person.

2. The measuring device as claimed in claim 1 wherein said anthropometric characteristics include spine curvature of the person determined by calculating the radius of curvature by taking chords between three vertically adjacent points on the side view image of the illumination strips.

3. The measuring device as claimed in claim 1 wherein the illumination strips are operable to generate light of a particular colour and the camera is adapted to be preferentially sensitive to said colour.

4. The measuring device as claimed in claim 1 wherein the illumination strips are adapted to blink at a specified frequency and the computer is operable to compare an image received from the camera when the illumination strips are illuminated with an image received from the camera when the illumination strips are not illuminated in order to eliminate extraneous detail from the image resulting from ambient light.

5. The measuring device as claimed in claim 3 wherein the illumination strips are adapted to blink at a specified frequency and the computer is operable to compare an image received from the camera when the illumination strips are illuminated with an image received from the camera when the illumination strips are not illuminated in order to eliminate extraneous detail from the image resulting from ambient light.

6. The measuring device as claimed in claim 1 wherein the support frame is an upstanding frame and a plurality of horizontal illumination strips are mounted vertically spaced-apart on the support frame.

7. The measuring device as claimed in claim 1 wherein the camera is a personal computer web cam connected to a computer via USB.

8. The measuring device as claimed in claim 1 wherein the illumination strips comprise electroluminescent wires.

9. The measuring device as claimed in claim 1 wherein the illumination strips comprise fluorescent strip lights.

10. A method for determining individual user anthropometric characteristics related to mattress preference to aid mattress selection, including:
    positioning said user in a front view between a set of spaced-apart illumination strips and a camera,
    illuminating said illumination strips,
    taking an image of the illuminated strips and said user by means of the camera,
    delivering said image from the camera to an associated computer,
    positioning said user in a side view between the set of spaced-apart illumination strips and the camera,
    illuminating said illumination strips,
    taking an image of the illuminated strips and said user by means of the camera,
    delivering said image from the camera to the associated computer, and
    determining by means of said computer one or more preselected anthropometric characteristics of the user based on those portions of said images of the illuminated strips blocked by the person standing between the camera and the illuminated strips in said front view and said side view and the distance between said illuminated strips, said anthropometric characteristics including body mass distribution determined by delineating a series of polygons characterising the body shape of said person.

* * * * *